US00PP09101P

United States Patent [19]

Schreurs

[11] Patent Number: Plant 9,101

[45] Date of Patent: Apr. 11, 1995

[54] FLORIBUNDA ROSE PLANT NAMED FLEUR

[75] Inventor: Petrus N. J. Schreurs, De Kwakel, Netherlands

[73] Assignee: Piet Schreurs de Kwakel B.V., PD De Kwakel, Netherlands

[21] Appl. No.: 246,747

[22] Filed: May 20, 1994

[51] Int. Cl.[6] ..... A01H 5/00

[52] U.S. Cl. ..... Plt./26

[58] Field of Search ..... Plt. 26, 27

*Primary Examiner*—Howard J. Locker

*Attorney, Agent, or Firm*—Foley & Lardner

[57] ABSTRACT

A new rose plant of the Floribunda Class named Fleur, characterized by good flower production even in winter; small, pink, simultaneously opening flowers borne in clusters; 3 to 5 flowers per cluster; flowers with 25 to 35 petals; small to medium stem length; vigorous upright growth; a vaselife of about 12 days; and more than 90% of the flowering stems have flowers borne in clusters.

4 Drawing Sheets

The present invention comprises a new and distinct cultivar of rose plant of the Floribunda Class, hereinafter referred to by the cultivar name Fleur.

Fleur is a product of a planned breeding program having the objective of creating new Floribunda Class rose cultivars with characteristics ideally suited for the production of cut flowers; good production of small, pink, simultaneously opening flowers borne in clusters; production of more than 90% sprays throughout the year, which is understood to mean that more than 90% of the flowering stems have flowers borne in clusters (perfect spray rose) and less than 10% of the flowering stems have only one single flower ('normal' rose type); and a vigorous upright growth habit.

Fleur was originated from a hybridization made by Petrus N. J. Schreurs in a controlled breeding program in De Kwakel, The Netherlands, in 1987. The female parent was an unnamed Piet Schreurs De Kwakel seedling having red flowers. The male parent was an unnamed Piet Schreurs De Kwakel seedling having small white flowers requiring frequent pinching.

Fleur was discovered and selected as one flowering plant within the progeny of the stated parentage by Petrus N. J. Schreurs, in February, 1988 in a controlled environment in De Kwakel, The Netherlands. Asexual reproduction of the new cultivar by budding and cuttings, as performed by Petrus N. J. Schreurs in De Kwakel, The Netherlands, demonstrated that the combination of characteristics, as herein disclosed for Fleur, are firmly fixed through successive generations of asexual reproduction.

Fleur has not been observed under all possible environmental conditions. The phenotype may vary significantly with variations in environment, such as temperature, light intensity, and daylength, without any change in genotype.

The following observations, measurements and comparisons describe plants grown in De Kwakel, The Netherlands under greenhouse conditions which approximate those generally used in commercial practice. The following traits have been repeatedly observed and are determined to be basic characteristics of Fleur, which in combination, distinguish this rose as a new and distinct cultivar:

1. Vaselife of 12 days.
2. Good flower production throughout the year.

3. Small, pink, simultaneosuly opening flowers borne in clusters.
4. Flowers are in clusters, with 3–12 flowers per stem.
5. Flowers having 25 to 35 petals.
6. Small to medium stem length.
7. Fleur can be cultivated with or without rootstock.
8. No unusual susceptibility to fungal pathogens.
9. Impressively fast start and fast growth, with a relatively short time between planting and first production.
10. Vigorous upright growth habit.
11. More than 90% of the flowering stems have flowers borne in clusters throughout the year.

Of the many commercial cultivars known to the present inventor, the most similar in comparison to Fleur is Interniki, a red spray rose described in U.S. Plant Pat. No. 8,114. Chart A compares certain characteristics of Fleur to those same characteristics of Interniki.

In general comparison to Interniki, Fleur has a different flower color; longer average stem length; smaller leaves that are lighter in color and weaker, and fewer petals. Fleur's leaves are softer, and if there is insufficient water after cutting Fleur's leaves dry up faster than Interniki.

The accompanying color photographic drawings show the typical inflorescence and foliage characteristics of Fleur, with colors as nearly true as possible with illustrations of this type.

Sheet 1 is a single stem of Fleur.

Sheet 2 is a comparison of one stem of Fleur and Interniki.

Sheet 3 shows an area planted with Fleur.

Sheet 4 is a comparison of different plant parts from Fleur and Interniki.

The photos were made in De Kwakel, The Netherlands in a greenhouse with a light intensity of about 2.40 Klux.

In the following description, color references are made to The Royal Horticultural Society Colour Chart. The color values were determined between 10:00 a.m. and 12:00 noon on May 7, 1992, under 2.40 Klux, in De Kwakel, The Netherlands.

Classification:

*Botanical*—*Rosa Hybrida*, cv. Fleur.

*Commercial*—Floribunda, spray rose.

Plant:

*General appearance.*—Habit: Upright growth habit, thorns are pointed down, the top of the thorn is straight and the under side is concave. Growth: Vigorous, medium height of approximately 90 to 120 cm at maturity. Canes: Small to medium length. Main stems: Small to medium length. Thorns: Typical size and number on main stems and canes. Branches: New wood is light green and smooth, old wood is green, frequently brown longitudinal stripes of bark.

*Foliage.*—Leaves: Number: Normal mid-stem leaves have 5 to 7 leaflets. Shape: Pointed oval shape. Appearance: Dull, smooth texture with serrated edge; serration is single and small in size. Color (top side): R.H.S. 138A. Color (bottom side): Whitish green. Petioles: Rachis is green and red, the underside of petiole is smooth, with few thorns, stipules are very short and bearded. Other foliage characteristics: New foliage is reddish in color.

Flowers:

*Borne.*—In clusters with 3 to 5 flowers per cluster.

*Number of flowers (per stem).*—3 to 12.

*Quantity of blooms.*—Continuous blooming habit.

*Buds.*—Peduncle: Small with smooth surface and stiff, erect small thorns, color is medium green. Size: 1 cm when petals begin to open; the closed bud is a short pointed ovoid. Color: The bud color at calyx break is R.H.S. 49A. Sepals: 1 to 3 lightly appendaged sepals and 2 unappendaged sepals. Blooms: Size: Small, with average open diameter of 5 to 5.5 cm. Petalage: Number: 25 to 35 per flower. Length: 1 to 2 cm. Texture: Thick. Shape: Deltoid with slight recurved tips; when the flower first opens, it has a high center which is retained; outer petals curl back with some quilling; petal arrangement is imbricated, with few petaloids in center. Color: Upperside: R.H.S. 48D, large white triangular spot from point of attachment to half the length of the petal; the white spot is on both the upper and under side of the petal. Underside: R.H.S. 49A.

*Fragrance.*—None.

*Reproductive organs.*—Stamens: Many of medium size, arranged regularly around styles. Filaments: White. Anthers: Yellow. Pollen: Yellow to light brown. Pistils: Greenish-white. Styles: Greenish-white. Ovaries: Greenish-white. Hips: Small, with a diameter of approximately 1.5 cm, round, turn from green to yellow to orange as they ripen.

Disease resistance: The foliage exhibits typical susceptibility in De Kwakel, The Netherlands to powdery mildew under normal growing conditions. Fleur is a greenhouse cut flower variety and, therefore, has not been tested for black spot or rust resistance.

I claim:

1. A new and distinct variety of rose plant named Fleur, as illustrated and described.

* * * * *

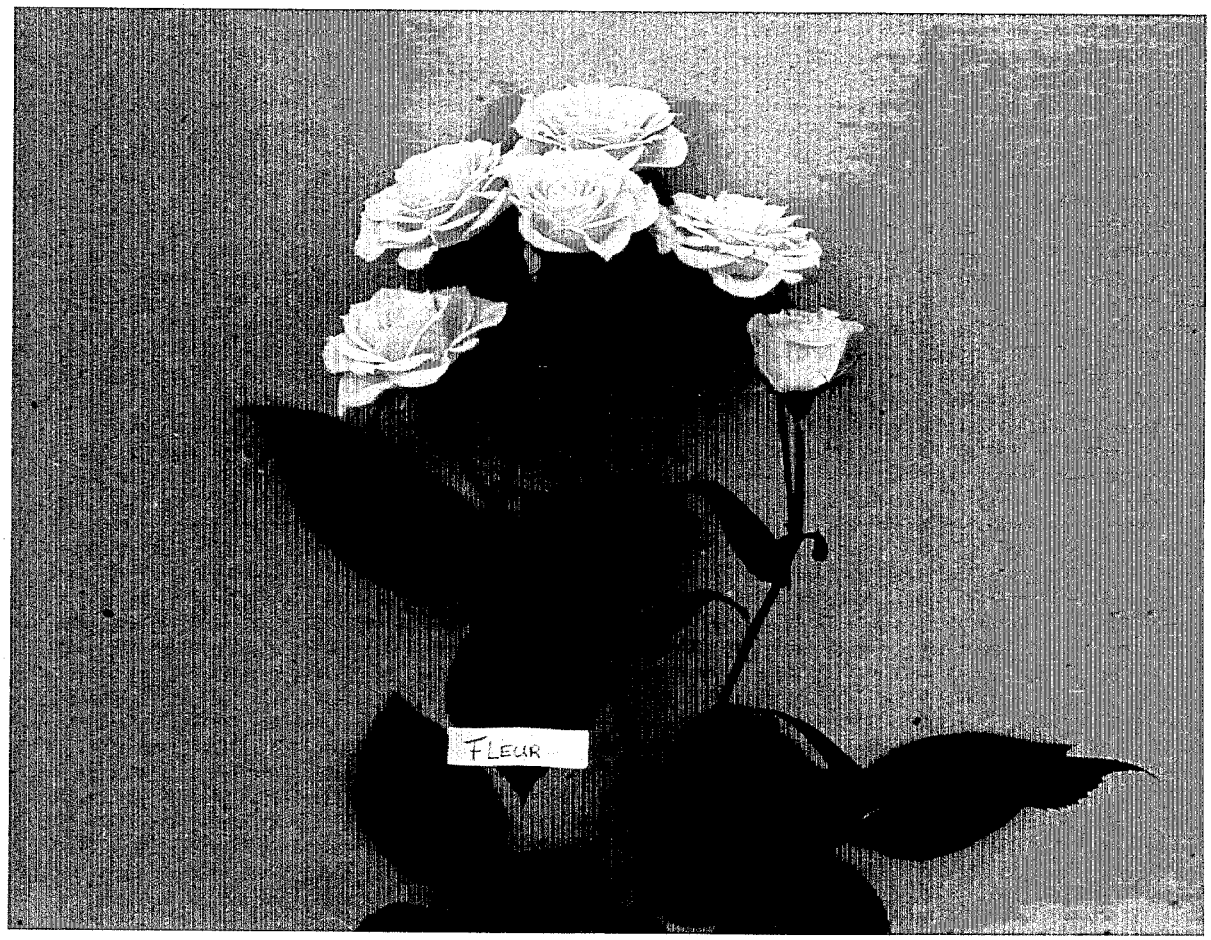
FLEUR

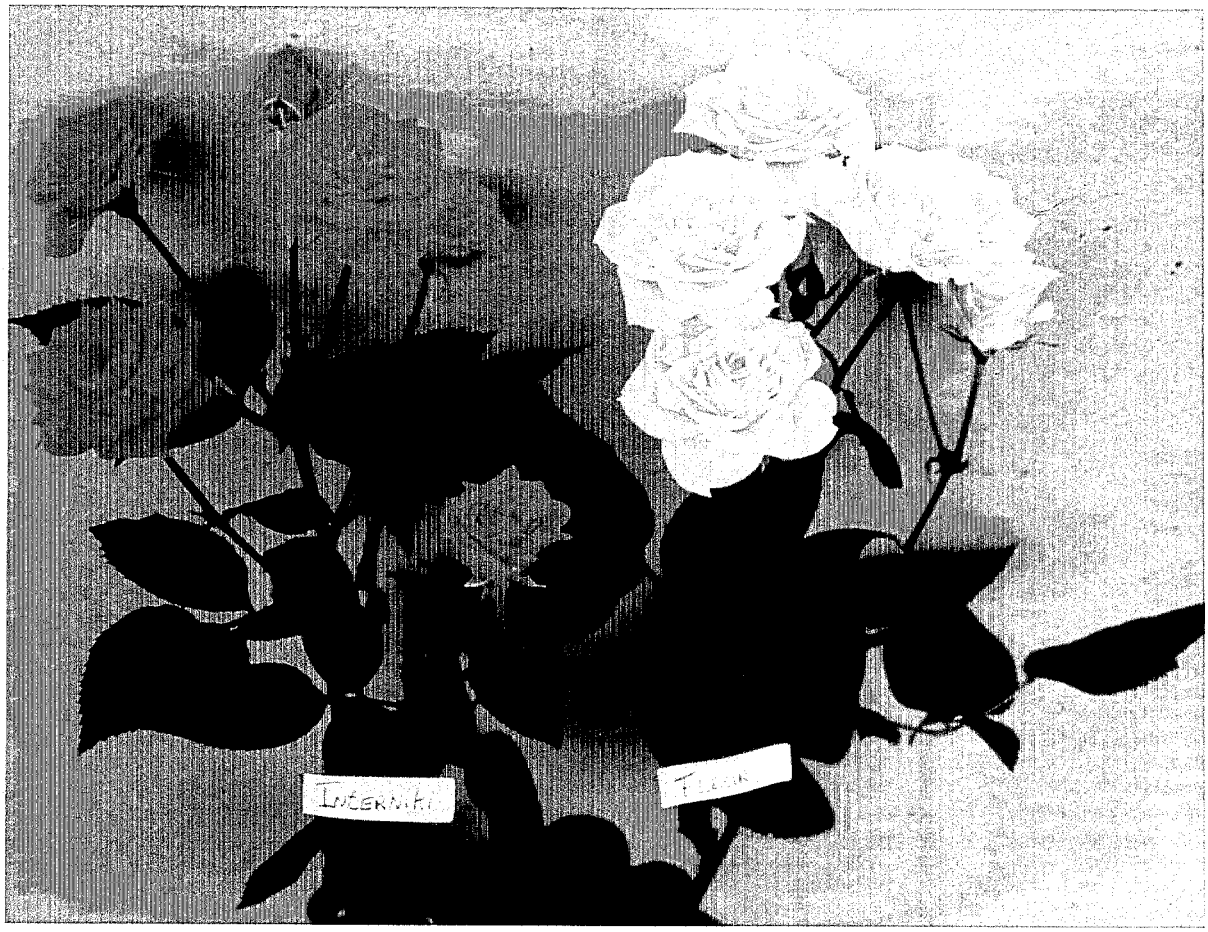
INGERNIKI

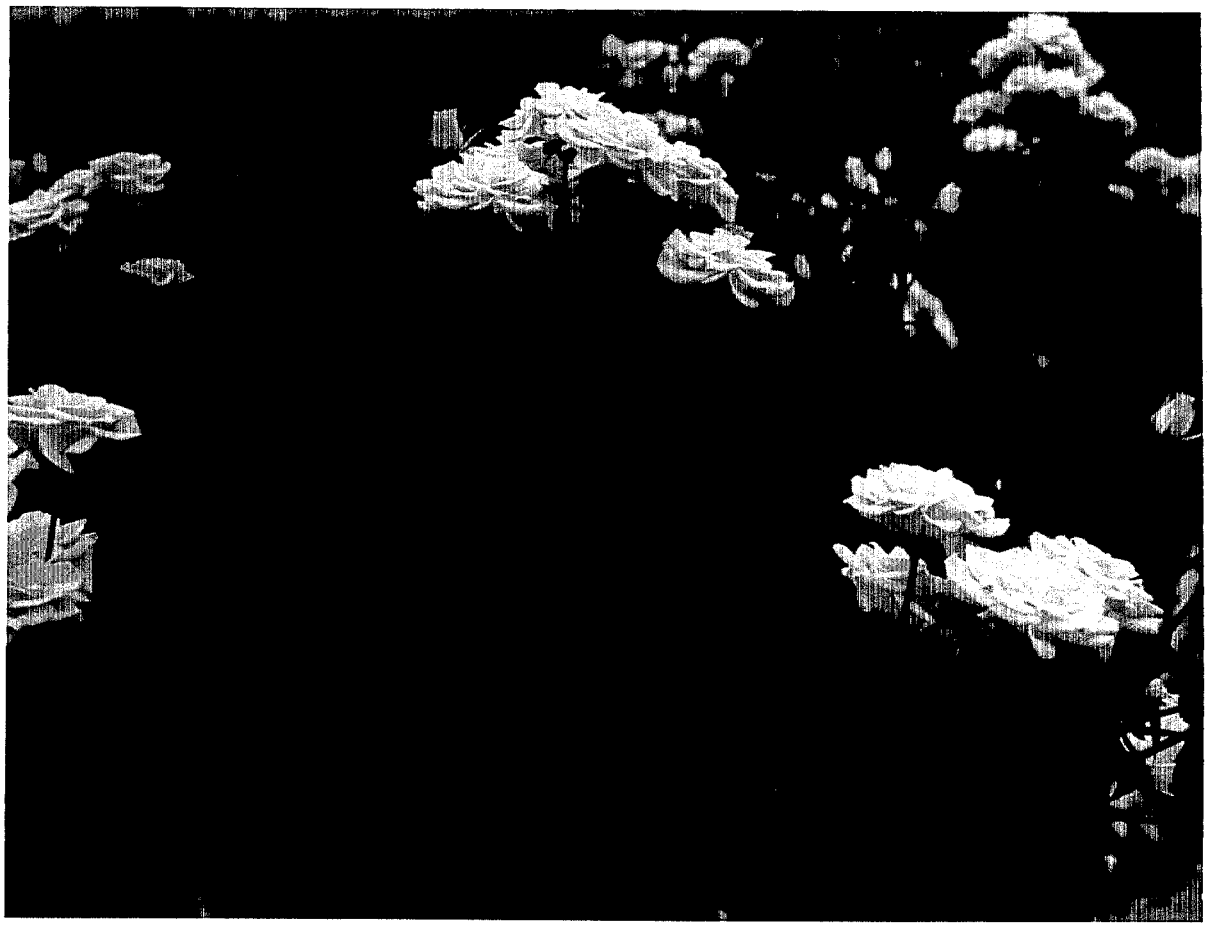

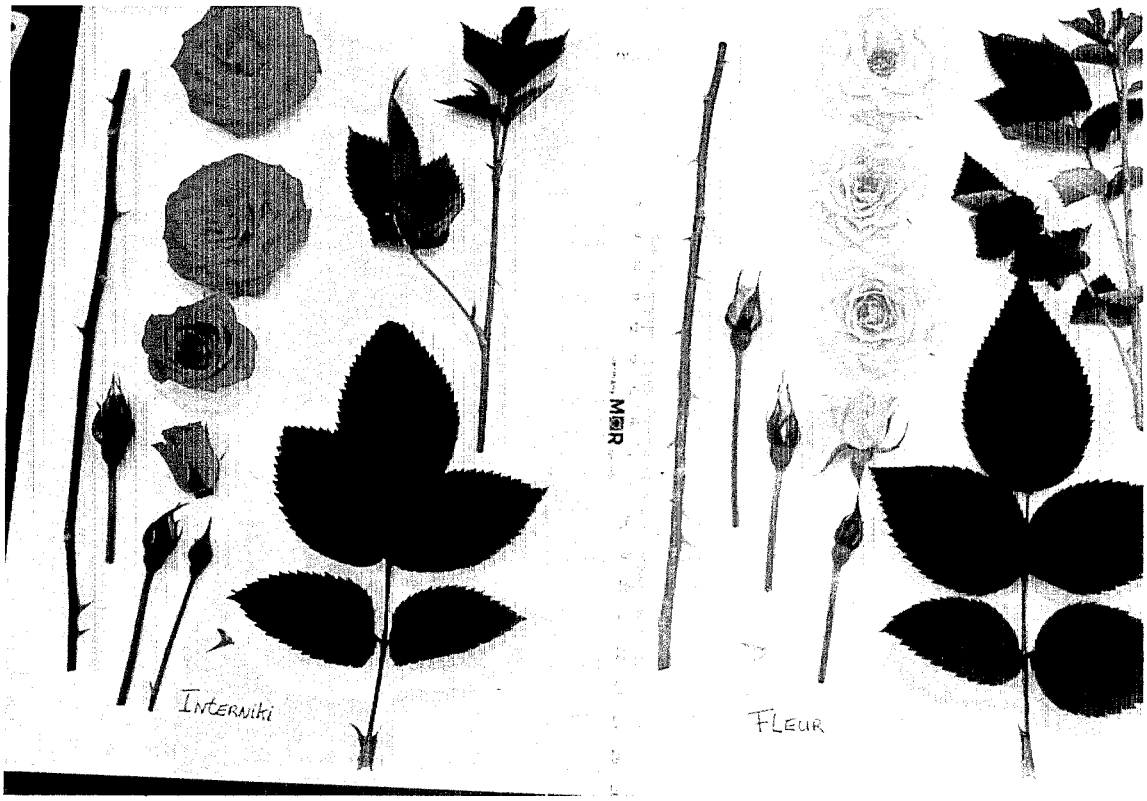
FLEUR
M&R
INTERNIKI